(12) United States Patent
Innerst et al.

(10) Patent No.: US 7,189,354 B2
(45) Date of Patent: Mar. 13, 2007

(54) OPTICALLY AND FLUIDICALLY ENHANCED IN VITRO DIAGNOSTIC TEST CHAMBER

(75) Inventors: Dianna Innerst, San Jose, CA (US); Adonis Kassinos, San Jose, CA (US); C. Benjamin Wooley, Chapel Hill, NC (US); Brett Wilmarth, Tracy, CA (US); William J. Sell, Petaluma, CA (US); Emi Zychlinsky, Palo Alto, CA (US); Donald Marino, Scotts Valley, CA (US); Sandy Yamada, San Jose, CA (US); Renee Ryan, San Jose, CA (US); Karen Ding, Fremont, CA (US); Michael Zatzke, San Jose, CA (US)

(73) Assignee: Hitachi Chemical Diagnostics, Inc., Mountain View, CA (US)

( * ) Notice: Subject to any disclaimer, the term of this patent is extended or adjusted under 35 U.S.C. 154(b) by 424 days.

(21) Appl. No.: 10/221,527

(22) PCT Filed: Mar. 20, 2001

(86) PCT No.: PCT/US01/09100

§ 371 (c)(1),
(2), (4) Date: Mar. 5, 2003

(87) PCT Pub. No.: WO01/71345

PCT Pub. Date: Sep. 27, 2001

(65) Prior Publication Data

US 2004/0071596 A1 Apr. 15, 2004

Related U.S. Application Data

(60) Provisional application No. 60/191,324, filed on Mar. 21, 2000.

(51) Int. Cl.
*G01N 21/00* (2006.01)
*G01N 31/22* (2006.01)
*G01N 15/06* (2006.01)
*G01N 33/00* (2006.01)
*C12Q 1/68* (2006.01)

(52) U.S. Cl. .................. 422/55; 422/50; 422/52; 422/56; 422/68.1; 422/81; 422/82.05; 422/82.06; 422/82.07; 422/82.08; 422/82.09; 422/82.11; 422/102; 422/103; 422/104; 436/43; 436/63; 436/164; 436/165; 436/169; 436/172; 73/1.01; 73/1.02

(58) Field of Classification Search .................. 422/50, 422/52, 55, 56, 57, 58, 68.1, 81, 82.05, 82.06, 422/82.07, 82.08, 82.09, 82.11, 102, 103, 422/104; 436/43, 63, 164, 165, 169, 172; 73/1.01, 1.02
See application file for complete search history.

(56) References Cited

U.S. PATENT DOCUMENTS

| | | | |
|---|---|---|---|
| 4,284,725 A | | 8/1981 | Fennel, III et al. |
| 4,459,360 A | | 7/1984 | Marinkovich |
| 4,567,149 A | | 1/1986 | Sell et al. |
| 4,956,150 A | * | 9/1990 | Henry .................. 422/102 |
| 5,244,630 A | | 9/1993 | Khalil et al. |
| 5,281,540 A | | 1/1994 | Merkh et al. |
| 5,447,837 A | * | 9/1995 | Urnovitz .................. 435/5 |
| 5,550,063 A | | 8/1996 | Bogart |
| 6,908,770 B1 | * | 6/2005 | McDevitt et al. ........... 436/518 |

FOREIGN PATENT DOCUMENTS

| | | |
|---|---|---|
| DE | 19647644 A1 | 5/1998 |
| WO | WO 86/06488 A1 | 11/1986 |
| WO | WO 99/52633 A1 | 10/1999 |

* cited by examiner

*Primary Examiner*—Brian Sines
(74) *Attorney, Agent, or Firm*—Townsend and Townsend and Crew, LLP

(57) ABSTRACT

An enclosed chamber is used in a system for screening of a liquid specimen through binding assays. The enclosed chamber includes an inlet, an outlet, and a plurality of discrete reactant containing wells communicated by a common reagent flow path between the inlet and the outlet. A transparent member or coverslip defines on an inside thereof the plurality of wells. Each well has a bottom for receiving an allergent/antigen/reactant, which emits light upon reacting. The coverslip can optionally define at least one lens at each well. A bottom encloses the plurality of wells and defines between the inlet and the outlet a common reagent flow path between the inlet and the outlet. This bottom defines for each of the plurality of wells a flow-diverting member. An opaque partition is disclosed for surrounding the individual lenses and generally isolating the light path from each well.

19 Claims, 6 Drawing Sheets

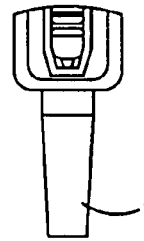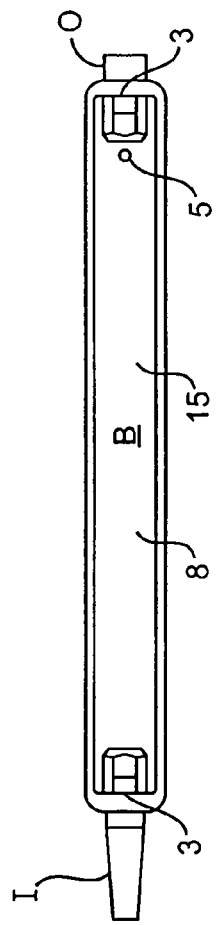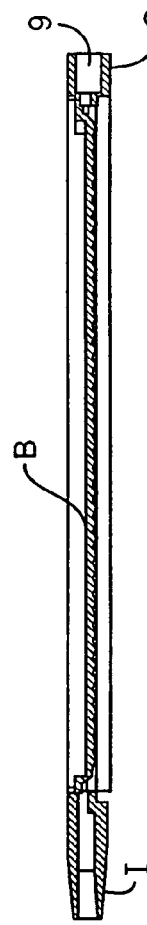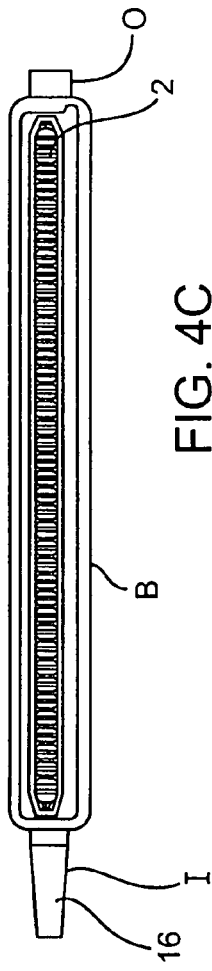

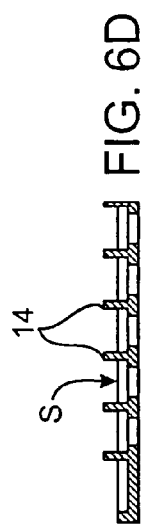
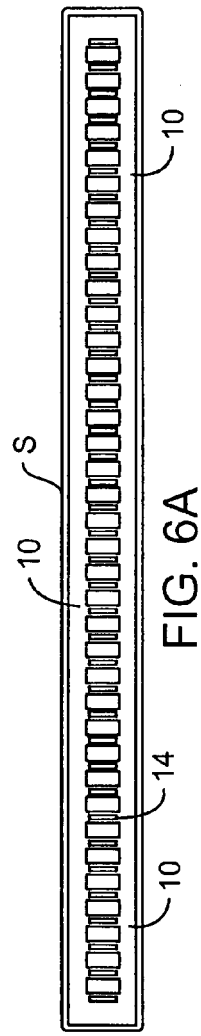
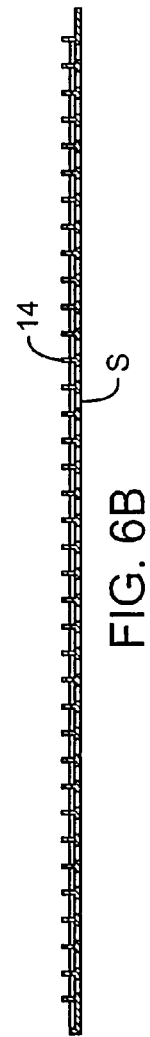
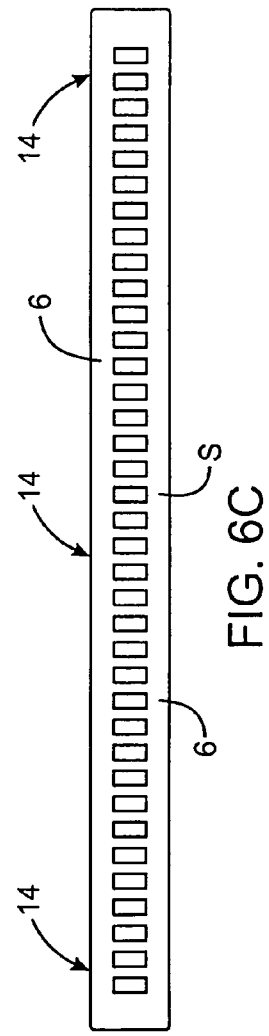
FIG. 6D
FIG. 6A
FIG. 6B
FIG. 6C

OPTICALLY AND FLUIDICALLY ENHANCED IN VITRO DIAGNOSTIC TEST CHAMBER

RELATED PATENT APPLICATION

This application claims priority from US Provisional Patent Application Ser. No. 60/191,324 filed Mar. 21, 2000 and entitled OPTICALLY AND FLUIDICALLY ENHANCED IN VITRO DIAGNOSTIC TEST CHAMBER by the inventors herein.

This invention relates to an apparatus and method for use in the diagnostic analysis of a liquid specimen through binding assays. More particularly, an optically and fluidically enhanced in vitro diagnostic test chamber and process of chamber utilization is disclosed over the apparatus and method disclosed in Sell et al U.S. Pat. No. 4,567,149 issued Jan. 28, 1986.

BACKGROUND OF THE INVENTION

In Sell et al U.S. Pat. No. 4,567,149 issued Jan. 28, 1986, an apparatus and a related method for use in the diagnostic analysis of a liquid specimen through binding assays was disclosed. The apparatus included a rigid body and a plurality of elongated threads, sometimes also referred to as filaments and/or strips, each coated with a binding assay component and supported on the body in spaced relationship for simultaneous contact with a liquid specimen. The plurality of elongated threads was positioned across an elongated well formed in the rigid body, generally transverse to the well's longitudinal axis. A transparent member, hereafter referred to as a coverslip, secured to the rigid body enclosed the elongated well between an inlet and an outlet along a common reagent flow path from inlet to outlet. The threads were protected during handling of the apparatus.

In use, a specific volume of the liquid specimen could be confined and isolated in the well, where it can incubate with the threads. The apparatus of the invention was particularly suited for allergy screening, with each elongated thread being a cotton thread coated with a specific allergen.

The rigid body used in Sell et al preferably was formed of plastic and included a flat land surrounding the elongated well. The thread was tensioned across the well, from lands on opposite sides of the well. The coverslip overlaid the threads and was secured to the lands on opposite sides of the well. To facilitate insertion of various liquids into the well, including the liquid specimen to be tested, suitable washing solutions, and a labeled antibody solution, the rigid body included a port at each end of the elongated well. The apparatus further included a pipette projection in alignment with the port located at one end of the well.

The coverslip preferably included a thin plastic sheet in direct contact with the land of the rigid body. The coverslip had an overlaying a silk screen having a series of parallel narrow apertures, each aligned with a separate one of the cotton threads. The silk screen optimizes the measuring of the reaction of each cotton thread by reducing the interfering effects of adjacent threads. The coverslip was preferably secured to the land of the rigid body by an ultrasonic weld.

The Sell et al U.S. Pat. No. 4,567,149 device is widely accepted and still in successful use. In use, the support and threads are filled and incubated with a liquid specimen, such as human sera. A secondary antibody (for example antibody conjugated to horse radish peroxidase—which reacts with luminol)—is incubated for about four hours. Thereafter, the threads were washed with a buffer—a saline solution and drained. This washing occurred three times. After this step, a fluid, which induces a chemiluminescent reaction, is introduced. The amount of multiple biological agents interacting with the binding assay components coated on the threads is determined by noting the presence and absence of light being emitted from each of the wells. For example, when screening for the presence of multiple allergen-specific IgE class antibodies in a liquid sample, the device is incubated with the test sample and then, after washing, incubated with a solution containing labeled antibodies against the IgE class antibodies that have bound to the threads. The threads are then analyzed to determine the presence of the labeled antibodies. If the labeled antibodies are labeled with a radioactive tracer, such as $^{125}$I, this analysis can be accomplished using a gamma counter. Alternatively, the analysis can be accomplished by placing the threads adjacent to photographic film for exposure and by then measuring the degree of exposure or more recently by registration to a light detector, either fiber optic or by direct detection.

This device has experienced a high degree of commercial success. This disclosure is an improvement on that device. Specifically, we have undertaken a systematic and extensive analysis of this prior art device. In what follows, the reader will have enumerated the specific areas for improvement.

It is to be understood that we claim invention in both determining the following areas for improvement as well as the specific solutions, which we have adopted in this disclosure. It is well understood that the identification of issues to be resolved, as well as their solution, can constitute invention. Therefore, in so far as the prior art has not identified the issues we now enumerate, with the device of Sell et al U.S. Pat. No. 4,567,149, invention is claimed.

DISCOVERIES

First, Sell et al U.S. Pat. No. 4,567,149 device had an elongate shallow well or channel which was uniform in cross-section, only interrupted by the threads that crossed the chamber. This resulted in a device, which required approximately 1.5 milliliters of serum to produce the desired test result. Unfortunately, pediatric samples in most cases are of a lesser volume. For example, it was determined that a device requiring 0.500 milliliters or less would have greater utility, especially in the pediatric field.

Secondly, it has been determined that threads in general, and especially cotton threads, require large volumes of allergen/antigen/reactant in their absorption. For example, 40 milliliters of allergen extract was required to coat 12 yards of thread which could be used as one of 600 threads in the units of the device of Sell et al U.S. Pat. No. 4,567,149. This rate of usage increases the cost of the test, as it requires very large-scale allergen extraction. This is a disadvantage because it increases the cost of the product. Additionally, the thread is a natural product (cotton) and it can be difficult and costly to control in quality from lot to lot.

As will hereafter be disclosed, this same 40 milliliters of allergen may now be used for 20,000 tests! The new design has allergens directly attached to the polystyrene coverslip and no thread is used.

Third, the alignment and registry of the individual threads between in the individual lands of the device required constant attention and effort. Misalignment had to be avoided to prevent "false positive" or "false negative" reactions.

Fourth, and once the threads have been incubated with reactants—such as serum—it is required that they be washed and drained. With a straight flow path, washing of threads requires excessive fluid. Further, cotton threads utilized provided both resistance to uniform washing as well as encouraging fluid retention of the human sera or saline solution. Specifically, at the juncture of the threads and flow path, residual solution—either the sera or the saline solution—tended to accumulate. This accumulation occurred due to the combination of surface tension combined with the irregular surfaces provided where the threads entered the channel of the device. Specifically, the cotton threads introduced additional salient features (surfaces) where fluid could be entrapped by surface tension (capillary forces). The operator is currently expelling this fluid manually.

The device is currently used for in vitro testing of immune reactions to various allergens. From a fluid mechanics prospective, the operation of the device requires that blood serum be aspirated into the test chamber where it comes in contact with the various allergens deposited into the threads. The serum is subsequently drained (under gravity) from the test chamber and a saline solution is used to further wash the device. During the washing cycle, a nozzle is inserted into the inlet atop the device, forming a hermetic seal that enables fluid to be injected under pressure into the test chamber. When this seal is broken by the removal of the nozzle, the resulting pressure vacuum is alleviated, which allows the fluid to drain from the device. The incomplete or even inconsistent draining of the washing solution from the test chamber represents a potential dilution problem for the subsequent operation of the device, requiring the operator to ensure that all fluid is expelled from the chamber after washing.

Fifth, the light output from the device indicating a reaction could be improved upon. Specifically, threads exhibiting a very high reaction could radiate light outside of its readable area, necessitating the use of a quenching reagent. Further and where a reaction was extraordinarily weak, an increase in substrate was needed.

Sixth, the coverslip is made of extruded polystyrene, which is prone to scratches and is difficult to manufacture necessitating QA efforts to select parts. Even though the scratches are only cosmetic defects, a molded part would eliminate them and be more cost effective.

In short, our detailed study made clear that improvement was possible.

SUMMARY OF THE INVENTION

An enclosed chamber is used in a system for screening of a liquid specimen through binding assays. The enclosed chamber includes an inlet, an outlet, and a plurality of discrete reactant containing wells communicated by a common reagent flow path between the inlet and the outlet. A transparent member or coverslip defines on an inside thereof the plurality of wells. Each well has a bottom for receiving a reactant, which emits light upon reacting. The coverslip further defines between the bottom of the plurality of wells and the exterior of the coverslip a light path for detection of the reaction. This coverslip can optionally define at least one lens at each well and is a molded part. This light path re-emits light from reactions within the well to the exterior of the coverslip indicating the absence of or presence of a reaction. A bottom member defines for each of the plurality of wells a flow-diverting member. The flow-diverting member is a continuous surface, the continuous surface protruding to and toward one of the plurality of wells for deflecting fluid flowing from the inlet to the outlet into the interior of the wells. This deflection permits washing of fluids from the plurality of wells. At the same time, the continuous surface enhances and substantially improves fluid draining of the flushing solution—usually a saline solution. Where a solution having either the emission or absence of light is utilized to indicate reaction, the light path and optional lenses serve both to concentrate the light emitted as well as to inhibit false positive indications. Finally, an opaque partition with slits is disclosed for surrounding the individual lenses and generally isolating the light path from each well. Improved detection results.

With the assembly of a coverslip, a bottom member and an opaque partition, a chamber that uses a low volume of patient serum results. The present chamber is filled by approximately 270 µl of liquid. The chamber is especially useful in the case of pediatric samples. At the same time, the reduction in volume does not result in poor washing characteristics. The fluidic design of the chamber allows for the use of small volumes of patient sera as well as insures sufficient washing.

The internal test chamber with its flow augmentation features has been designed, based on Fluid Mechanics principles, to optimize the washing of the allergen wells and the draining characteristics of the device. The shape, size, and placement of (a) the allergen cavities, (b) the flow augmenting "continuous surface", and (c) the chamber inlet/outlet sections have been selected to: (1) minimize the internal volume of the test chamber, (2) reduce capillary fluid retention during draining, (3) maintain optimal washing of the allergen cavities at low and high flow rates, and, (4) allow for the efficient operation of the device over a wider range of positions.

The contoured "continuous surface" enhances the wash-ability of the device by re-directing the main channel flow into the allergen cavities. The device may be operated without significant loss in washing/draining efficiency up to 35 degrees offset from the nominal vertical position.

The migration from the flat coverslip toward the new allergen wells introduced new complexities into the design. Where draining was one of the major issues with the flat coverslip configuration, here the "wash-ability" of the device in the presence of the allergen cavities becomes the major area of concern. That is, the ability of the flow pattern induced by the injection of the washing solution into the chamber to displace the more viscous reagent or blood serum from the surfaces and corners of the allergen cavities. Thus, the internal shape of the test chamber is designed to allow for sufficiently strong fluid flow to penetrate into these cavities and clean them out.

Strictly from a fluid mechanics prospective, it is desirable to have these cavities be as wide as possible in the direction of the flow and also as shallow as possible. However, the cavities must be sufficiently deep to allow for the deposit of the required amount of material to be tested, such as the allergen. Furthermore, the cavities cannot be made excessively wide without an adverse effect on the optics of the device, i.e. the ability of the light path and partition system (with or without the optional lens) to efficiently concentrate the light for detection and to isolate the emitted light from the adjacent wells. Therefore, the design of the allergen cavities has been carried out in a manner that satisfies the flow, optical, and chemical requirements of the device.

One of the changes needed was to design a chamber that could focus the light output. This change in design is important for three reasons. Firstly, the new chamber is designed to increase assay specificity when very high patient response is experienced. Secondly, the chamber is designed to increase assay sensitivity by focussing the light onto the detector system. Third, the light is no longer emitted from a line source such as thread. It is instead emitted from the flat bottom surface of a well.

From an optical perspective, the design goal is to develop an in vitro diagnostic test chamber that will allow the light emitted by multiple allergens placed within a chamber to be efficiently collected while obtaining minimum light crossover between these multiple allergens. The detection system that detects the light emission operates (as by scanning) along a line collecting light that enters its input aperture within a given angular range. In a detection device utilizing the prior art heretofore described, positioning the detection optic (it actually reads it as it scans past) collects the light from a single allergen at a particular location along its scan line. Essentially, because of the requirement to be backward compatible with the existing detection equipment, some of the chamber geometry is fixed. Two pieces, an optically absorbent main body and the optically transparent coverslip form the chamber.

The allergen is placed in spaced wells (which may or may not be equally spaced) directly onto the transparent coverslip. Typically the surface of the well where the allergen is placed can be treated by radiation, such as gamma or ultra violet. The depth of the wells and the shape of the tapered edges are determined as a tradeoff to minimize the light cross-over and maximize the washing capabilities. The top of the coverslip has a series of indentations between each of the wells that do not extend entirely through the piece. On the top of the coverslip is an optically opaque partition piece which has slots located directly above each allergen well. These slots allow light to pass through the lenses to the detector. The partition piece has fingers or individual opaque partitions with slits that extend into the indentations in the coverslip to block light from passing to the adjacent read area.

On top of the coverslip, directly above the wells that hold the allergens, is a series of equally spaced lenses. The lenses protrude into the slots in the partition and can have various shapes. By properly tailoring the curvature of the lenses the amount of light from each allergen that is collected and detected by the detection system can be optimized. This invention allows the lenses to have a cylindrical shape, a toroidal shape, or spherical surface profile to optimize the light collection efficiency.

BRIEF DESCRIPTION OF THE DRAWINGS

FIG. 4A is a bottom plan view of the bottom of the chamber body;

FIG. 4B is a side elevation section of the bottom of the chamber body;

FIG. 4C is a top plan view of the interior of the chamber body;

FIG. 4D is an end elevation section of the entrance to the chamber in the bottom of the chamber body;

FIG. 4E is a top plan view of the entrance in the bottom of the chamber body;

FIG. 6A is a bottom plan of the optical partition of the chamber;

FIG. 6B is a side elevation section of the optical partition of the chamber body;

FIG. 6C is a top plan of the optical partition of the chamber body; and,

FIG. 6D is an enlarged side elevation section taken at the optical partition.

DESCRIPTION OF THE SPECIFIC EMBODIMENTS

Figure 1A:
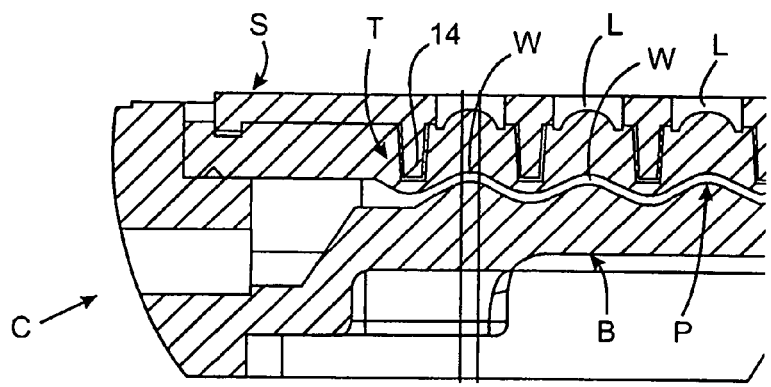
FIG. 1A is a side elevation section of the assembled in vitro diagnostic test chamber illustrating from bottom to top, the lower test chamber body, the common reagent volume; the upper coverslip defining the individual wells and lenses; and the overlying optical partition.

Referring to the side elevation section of FIG. 1A, an overall understanding of the assembled chamber C can be attained. Chamber C includes bottom B defining flow protrusions P. As will hereafter be set forth, it is the function of bottom B and flow protrusions P to provide an efficient cleansing action to the individual wells W containing the desired reactants R To aid in minimizing light carry-over, bottom B is made from a material, which absorbs light. We prefer the use of an opaque material that absorbs light as distinguished from materials, which in any way may be reflective.

Figure 1B:
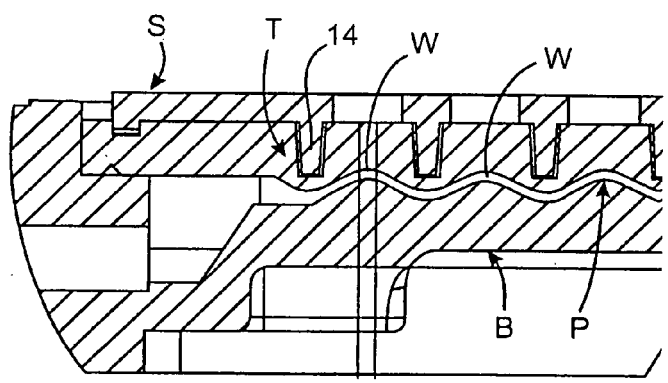
FIG. 1B is a side elevation section of the assembled in vitro diagnostic test chamber illustrating from bottom to top, the lower test chamber body, the common reagent volume; the upper transparent member defining the individual wells, light path without lenses; and the overlying optical partition.

Overlying bottom B and spaced apart from the bottom as shown in FIG. 1 is transparent member or coverslip T. Coverslip T serves three major functions. First and when inverted from the disposition shown in FIG. 1A and 1B, individual wells W receive reactants R. Reactants R adhere to the bottom of wells W when coverslip T is inverted. (See FIG. 2).

Second, transparent cover or coverslip T permits light to escape from reactants R in wells W when a diagnostic process is completed. Taking the example of a screen test for allergy, one or more of the wells W may emit light indicating the presence or absence of a specific type of allergic reaction.

Third, coverslip T defines lenses L in FIG. 1A, only. These lenses L are typically cylindrical, overly wells W and permit a generally collimated light beam B to escape from reactants R at the completion of a diagnostic reaction. In FIG. 1B, embodiment is shown which does not include lenses L.

Finally, and fitting around lenses L, opaque piece S is shown. Opaque piece S includes opaque partition with slits 14 that protrude on either side of the individual lenses L. It is the function of opaque partition with slits 14 to limit light from reactants R in one well W from giving a "false positive" indication. This can occur by the light escaping from one well to a lens L overlying an adjacent well W. The purpose of the opaque piece S is also to minimize the light that is emitted laterally from one well to intersect and then scatter from an adjacent well.

Figures 3A, 3B, 3C:
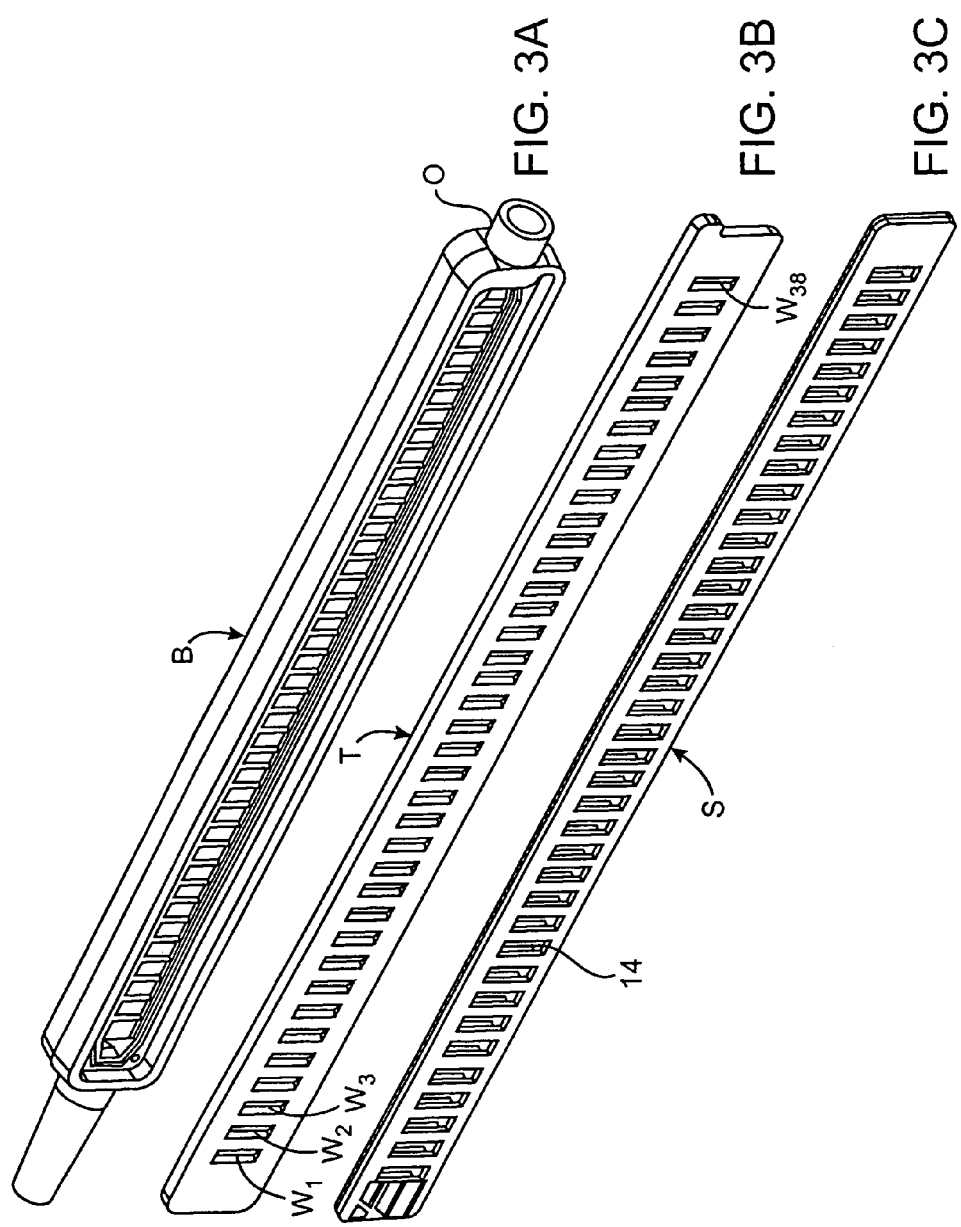
FIG. 3A is a perspective view of the bottom chamber member defining the continuous curvilinear protrusion between the inlet and outlet of the chamber of this invention.
FIG. 3B is a perspective view of the coverslip from the well side, it being realized that for assembly to occur rotation of the coverslip by 180° is required to occur.
FIG. 3C is a perspective view of the optical partition for overlying the individual lenses of each of the diagnostic wells.

Referring to the side-by-side perspectives of FIGS. 3A, 3B and 3C and with special attention to FIG. 3B, assembly of the diagnostic chamber of this invention can be easily understood. FIG. 3B illustrates coverslip T from the side containing the individual wells W. It begins with well W1 and ends with well W38. In the example here shown, wells W1, W2, and W3 have each been filled with a reagent R1, R2, and R3. In the normal course of events, coverslip T would be rotated 90° and have all thirty-eight wells filled, each one with a different reagent. Typically, each reagent would be treated until adherence to the bottom of wells W occurred. In the usual case, this will only require drying under controlled conditions. Once this adherence has occurred, coverslip T is reversed from the position shown in FIG. 3B so that lenses L (not shown) are toward the viewer.

The rest of the assembly is conventional. Coverslip T is fitted to bottom B in fluid tight relation. Between coverslip T and bottom B, a fluid tight volume is defined between inlet I and outlet O. Thereafter, opaque piece S is fitted over coverslip T at lenses L with opaque partition with slits 14 disposed on each side of each lens L. There results an assembled diagnostic test chamber C.

Use of chamber C can be outlined. In use, chamber C is filled through inlet I with outlet O open until fully filled with reagent—which is usually serum for detecting an allergic reaction. When filled, reactants R are incubated for a sufficient interval to indicate the presence and/or absence of a reaction.

A secondary antibody (for example an antibody conjugated to horseradish peroxidase—which reacts with luminol)—is then incubated. Thereafter, the wells W are washed with a saline solution and drained. This washing and draining utilizes flow protrusions P within the continuous reactant flow path.

After this step, a fluid, which induces a chemiluminescent reaction, is introduced, this chemiluminescent reaction occurs at wells W where reactants R have a reaction. (See FIG. 2) The amount of multiple biological agents interacting with the binding assay components coated on the wells W is determined by noting the presence and/or absence of light being emitted from each of the wells.

For example, when screening for the presence of multiple allergen-specific IgE class antibodies in a liquid sample, the device is incubated with the test sample and then, after washing, incubated with a solution containing labeled antibodies against the IgE class antibodies that have bound to the wells. The wells are then analyzed to determine the presence of the labeled antibodies. If the labeled antibodies are labeled with a radioactive tracer, such as $^{125}$I, this analysis can be accomplished using a gamma counter. Alternatively, the analysis can be accomplished by placing the device adjacent to photographic film for exposure and by then measuring the degree of exposure or more recently by registration to a light detector, either fiber optic or by direct detection.

Having described the overall operation, attention may now be directed to the flow dynamics and optics resulting from this disclosure.

The average shear stress, $\bar{\tau}$, along the cavity wall at the well bottom was optimized. This shear stress represents a measure of the force that the washing solution would be capable of exerting on reagent or serum fluid particles that lie along the bottom of the wells W.

Figure 2:
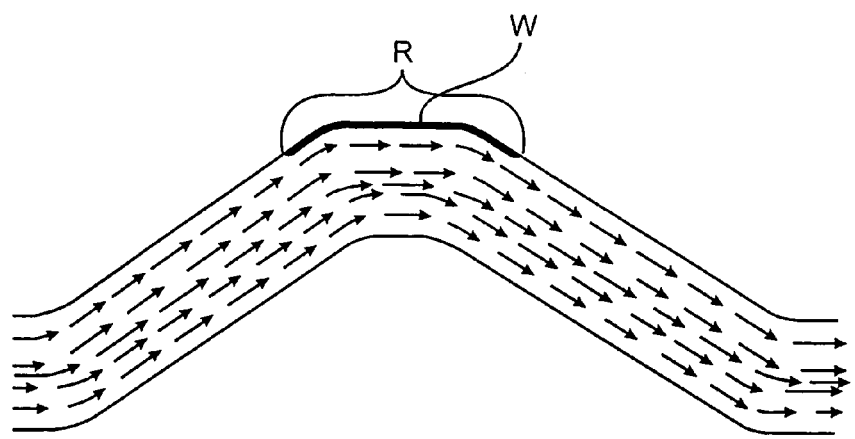
FIG. 2 is an enlarged diagrammatic representation of the action of the flow path deflecting a flushing flow interior of a well within the transparent coverslip.

Referring to FIG. 2, computer models for alternative configurations were constructed and used to obtain the flow pattern with the test chamber. The preferred embodiment resulting from these tests is shown in FIG. 2.

The magnitude of the resulting shear stress, averaged along the cavity wall, was computed and normalized against the base case. In the absence of any bumps on the bottom channel wall the "high-speed" main channel flow merely induces, as a result of shear (or friction) between the layers, a flow within the cavity. This flow is typically much weaker than the main channel flow. The most efficient flow, in terms of wall shear, occurs at an aspect (depth to width) ratio of approximately 0.5. If the cavity is too deep then the induced flow becomes too weak in the area adjacent to the top cavity wall. If the cavity is too shallow, it prevents the establishment of a well-organized flow pattern and the resulting wall shear begins to drop (note the decrease in $\bar{\tau}$, as the cavity depth decreases.

The preferred design for the well/protrusion configuration can be seen in FIGS. 1A and 1B. FIG. 2 sets forth an actual flow model illustrating fluid flow through the cavity of FIG. 4. While, dimensions are normally not important to invention, the design of the flow chamber here does have dimensional significance.

Referring to FIG. 1A and 1B, the depth of the flow channel is 0.011 inches. The channel inclines at a 27.4° angle upward and downward. The channel varies in elevation 0.020 inches. When viewed in plan the channel has an approximate width of 0.157 inches. The protrusion is centered with respect to well W. Total volume to fill the flow cavity is in the range of 270 µl.

In short, the geometry of the selected configuration has been determined based on numerous iterations that allowed for the successive improvement of the design concept. The basic cavity shape was changed from a rectangle to the top of a trapezoid.

Furthermore, the cavity walls better facilitate the draining of the device.

Assuming that a lens as set forth in FIG. 1A is used, optics through lens L must deliver relative low quantities of light to any particular test system used with the device. At the same time, light cross-over between a well W having reaction and an adjacent well not having a reaction must be prevented. We have discovered that the combination of the cylindrical lenses L with the flat well bottom of wells W produces a relatively collimated output of light from reaction. By constructing the bottom B and the opaque piece S from plastic opaque and absorbent to the light emitted (indicating the presence or absence of reaction), light cross-over is minimized.

It will be understood that the disclosed optics in combination with the well W represents a careful compromise that in large measure has been empirically determined.

Figure 5A:
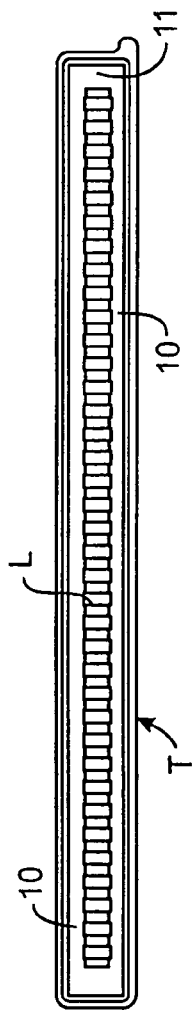
FIG. 5A is a top plan of the coverslip incorporating cylindrical lenses.
Figure 5B:
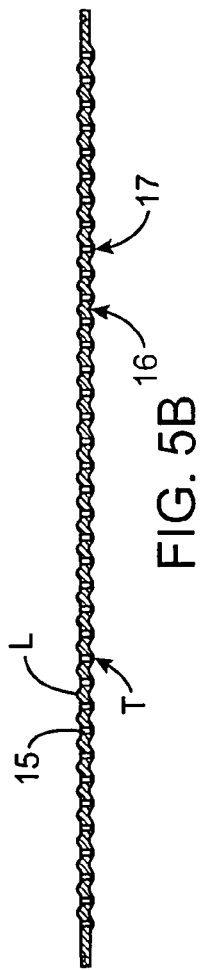
FIG. 5B is a side elevation of the coverslip illustrating the side elevation of the lenses.
Figure 5C:
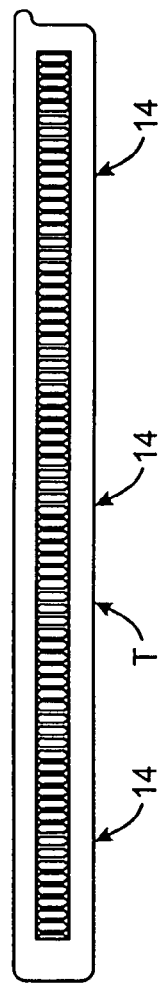
FIG. 5C is a bottom plan of the plate of FIG. 5A.
Figure 5D:
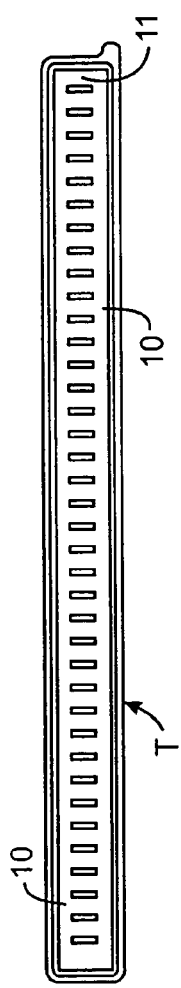
FIG. 5D is a top plan of the coverslip without lenses.
Figure 5E:
FIG. 5E is a side elevation of the coverslip without lenses.
Figure 5F:
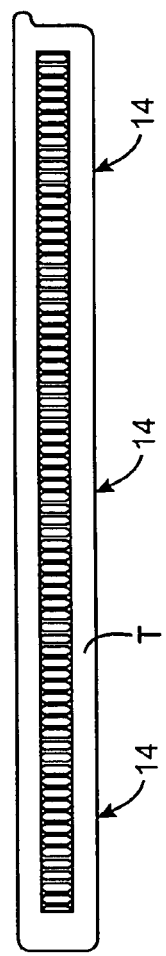
FIG. 5F is a bottom plan of the coverslip without lenses.

It has been emphasized that because of the relative small size and volume of the device that dimension is important. Accordingly, we provide the now preferred production drawings relating to the actual device as part of this disclosure. FIGS. 4A–4E illustrate the opaque bottom. FIGS. 5A–5C illustrate the coverslip T with cylindrical lenses incorporated to the design. FIGS. 6A–6D illustrate the optical partition. These are all provided so that the true dimensionality of this invention can be understood.

The reader should understand that we claim invention in at least two combinations. First, the interaction of the wells with the discrete lenses indicating the presence or the absence of a reaction within the discrete wells constitutes one portion of this invention. Secondly, the interaction of the wells within the continuous path constitutes another portion of this invention. For example, in certain protocols, it may be possible to open the device and expose the wells directly for the emission of light In this case, the interaction of the protuberances with the wells to assure a minimal volume of serum to promote the original reaction would constitute our invention.

We contemplate the use of all different kinds of labels for detected reactions. While we have enumerated $^{125}$I and chemiluminescent reactions, other forms of labels will do as well. For example, color metric enhanced reactions can be used. Further, while we set forth as our primary utility an allergic reaction, other types of reactions can be used as well. These other types of reaction can include detection of cancer markers, infectious diseases, hormones, autoimmune, and drug abuse.

What is claimed is:

1. In an enclosed chamber for use in a system for screening of a liquid specimen through binding assays, the enclosed chamber including an inlet, an outlet, and a plurality of discrete reactant containing regions communicated by a common reagent flow path from the inlet to the outlet, the apparatus comprising:
    a transparent member defining on an inside thereof a plurality of wells each having a bottom for receiving a reactant which emits light upon reacting;
    the transparent member further defining between the bottom of the plurality of wells and the exterior of the transparent member at least one lens at each well for emitting light from reactions within the well to the exterior of the transparent member;
    a bottom for enclosing the plurality of wells and defining between the inlet and the outlet a flow path connecting the plurality of wells into the common reagent flow path between the inlet and the outlet;
    the bottom defining for each of the plurality of wells a flow diverting member defining a continuous surface, the continuous surface protruding to and toward one of the plurality of wells for deflecting fluid flowing from the inlet to the outlet into an interior of the plurality of wells for permitting washing of fluids from the plurality of wells.

2. The enclosed chamber for use in a system for screening of a liquid specimen through binding assays according to claim 1 and further comprising:
    each of the plurality of wells includes a planar bottom over the chamber bottom.

3. The enclosed chamber for use in a system for screening of a liquid specimen through binding assays according to claim 1 and further comprising:
    each of the plurality of wells includes well sides defining obtuse angles to and toward the common reagent flow path from the inlet to the outlet.

4. The enclosed chamber for use in a system for screening of a liquid specimen through binding assays according to claim 1 and further comprising:
    each of the wells contains a coating from the group consisting of an allergens an antigen or a reactant.

5. The enclosed chamber for use in a system for screening of a liquid specimen through binding assays according to claim 1 and further comprising:
    a member defining optically opaque boundaries between the lenses for the wells to prevent light emitted from one reaction in one well from being transmitted to lens overlying a different well.

6. The enclosed chamber for use in a system for screening of a liquid specimen through binding assays according to claim 1 and further comprising:
    the common reagent flow path from the inlet to the outlet serially connects the plurality of wells.

7. In an enclosed chamber for use in a system for screening of a liquid specimen through binding assays, the enclosed chamber including an inlet, an outlet, and a plurality of discrete reactant containing regions communicated by a common reagent flow path from the inlet to the outlet, the apparatus comprising:
    a member defining on an inside thereof a plurality of wells each having a bottom for receiving a reactant;
    a bottom for enclosing the plurality of wells and defining between the inlet and the outlet a flow path connecting the plurality of wells into the common reagent flow path between the inlet and the outlet; and,
    the bottom defining for each of the plurality of wells a flow diverting member defining a continuous surface, the continuous surface protruding to and toward one of the plurality of wells for deflecting fluid flowing from the inlet to the outlet into an interior of the plurality of wells for permitting washing of fluids from the plurality of wells.

8. The enclosed chamber for use in a system for screening of a liquid specimen through binding assays according to claim 7 and further comprising:
    the depth of the well from the top of surface is 0.2 inches.

9. The enclosed chamber for use in a system for screening of a liquid specimen through binding assays according to claim 7 and further comprising:
    the common reagent flow path contains less than 300 microliters.

10. The enclosed chamber for use in a system for screening of a liquid specimen through binding assays according to claim 7 and further comprising:
    the flow-diverting member is centered with respect to the well.

11. The enclosed chamber for use in a system for screening of a liquid specimen through binding assays according to claim 7 and further comprising:
    the wells are treated with radiation at the well for retention of allergen/antigen/reactant placed in the well.

12. The enclosed chamber for use in a system for screening of a liquid specimen through binding assays according to claim 7 and further comprising:
    the member defining on an inside thereof a plurality of wells is transparent.

13. The enclosed chamber for use in a system for screening of a liquid specimen through binding assays according to claim 7 and further comprising:
    the member defining on an inside thereof a plurality of wells defines a lens overlying each of the wells for emitting light responsive to light being emitted from a reactant in the wells.

14. The enclosed chamber for use in a system for screening of a liquid specimen through binding assays according to claim 7 and further comprising:
    each of the plurality of wells includes a planar bottom.

15. The enclosed chamber for use in a system for screening of a liquid specimen through binding assays according to claim 7 and further comprising:
    each of the plurality of wells includes well sides defining obtuse angles to and toward the common reagent flow path from the inlet to the outlet.

16. The enclosed chamber for use in a system for screening of a liquid specimen through binding assays according to claim 7 and further comprising:

each of the wells contains a coated substance chosen from the group consisting of an allergen, an antigen and a reactant.

17. The enclosed chamber for use in a system for screening of a liquid specimen through binding assays according to claim 7 and further comprising:

the common reagent flow path from the inlet to the outlet serially connects the plurality of wells.

18. A process of screening of a liquid specimen through a series of binding assays between the inlet and outlet of an enclosed chamber; the process comprising the steps of:

providing a transparent member defining on an inside thereof a plurality of wells each having a bottom for receiving a reactant which emits light upon reacting;

depositing and adhering different reactants in different wells;

providing at least one lens at each well for emitting light from reactions within the well to the exterior of the transparent member;

providing a bottom for enclosing the plurality of wells and defining the inlet, the outlet, and a flow path between the inlet and the outlet connecting the plurality of wells into the common reagent flow path;

passing a reactant fluid from the inlet to the outlet to flood the common reagent flow path and react with reactants in the plurality of wells;

washing the reactant fluid from the wells by passing washing fluid from the inlet to the outlet over the continuous surfaces to enable washing of reagent from reactants in the plurality of individual wells; and, passing a reaction indicator through the enclosed passage from inlet to outlet, the reactant indicator having a luminescent reaction to indicate the presence and/or absence of reaction between the reactant and the reagent in the well.

19. A process of screening of a liquid specimen through a series of binding assays between the inlet and outlet of an enclosed chamber according to claim 18; the process comprising the further steps of:

defining for each of the plurality of wells a flow diverting member defining a continuous surface, the continuous surface protruding to and toward one of the plurality of wells for deflecting fluid flowing from the inlet to the outlet into an interior of the plurality of wells for permitting fluids to contact reactants within the wells.

* * * * *